(12) United States Patent
Christensen

(10) Patent No.: US 7,618,464 B2
(45) Date of Patent: Nov. 17, 2009

(54) PROSTHETIC FOOT WITH VARIABLE MEDIAL/LATERAL STIFFNESS

(75) Inventor: Roland J. Christensen, Fayette, UT (US)

(73) Assignee: Freedom Innovations, LLC, Irvine, CA (US)

( * ) Notice: Subject to any disclaimer, the term of this patent is extended or adjusted under 35 U.S.C. 154(b) by 568 days.

(21) Appl. No.: 11/499,863

(22) Filed: Aug. 3, 2006

(65) Prior Publication Data

US 2008/0033578 A1    Feb. 7, 2008

(51) Int. Cl.
A61F 2/66    (2006.01)
(52) U.S. Cl. ......................................................... 623/55
(58) Field of Classification Search ............... 623/47–56
See application file for complete search history.

(56) References Cited

U.S. PATENT DOCUMENTS

| | | |
|---|---|---|
| 42,799 A | 5/1864 | Shepard |
| 92,031 A | 6/1869 | Foster |
| 292,800 A | 2/1884 | Furrer |
| 497,026 A | 5/1893 | Judson |
| 1,001,641 A | 8/1911 | Harrison |
| 1,191,633 A | 5/1916 | Waggott |
| 1,289,580 A | 12/1918 | Vincenti |
| 1,779,765 A | 10/1930 | Eichhorn |
| 1,996,874 A | 4/1935 | Mascau |
| 2,036,830 A | 4/1936 | Rowley |
| 2,379,538 A | 7/1945 | Meierhofer |
| 2,443,356 A | 6/1948 | Mathis |
| 2,453,969 A | 11/1948 | Carter |
| 2,470,480 A | 5/1949 | Fogg |
| 2,570,735 A | 10/1951 | Weise |
| 2,617,115 A | 11/1952 | Ellery |
| 2,640,200 A | 6/1953 | Wisbrun |
| 2,843,853 A | 7/1958 | Mauch |
| 3,206,235 A | 9/1965 | Albernson |
| 3,548,420 A | 12/1970 | Spence |
| 3,551,914 A | 1/1971 | Woodall |
| 3,754,286 A | 8/1973 | Ryan |
| 3,858,379 A | 1/1975 | Graves et al. |
| 3,871,032 A | 3/1975 | Karas |

(Continued)

FOREIGN PATENT DOCUMENTS

BR    9304552    7/1995

(Continued)

OTHER PUBLICATIONS

MICA Manufacturing Corporation, Genesis II Prosthetic Foot, www.micacorp.com/products/genesis2/, 2004 Mica Manufacturing Corp.

(Continued)

*Primary Examiner*—Bruce E Snow
(74) *Attorney, Agent, or Firm*—Thorpe North & Western LLP

(57) ABSTRACT

A foot plate for a prosthetic foot includes a sole plate and a layer with laterally variable stiffness disposed above the sole plate. The layer has a medial portion and a lateral portion. The lateral portion has a stiffness different than a stiffness of the medial portion, such as a greater stiffness to provide a relatively softer instep and a relatively stiffer out-step.

21 Claims, 5 Drawing Sheets

U.S. PATENT DOCUMENTS

| | | |
|---|---|---|
| 3,874,004 A | 4/1975 | May |
| 3,906,552 A | 9/1975 | Weber |
| 3,920,610 A | 11/1975 | Wagner |
| 3,956,775 A | 5/1976 | Moore |
| 3,982,280 A | 9/1976 | Asbelle et al. |
| 4,089,072 A | 5/1978 | Glabiszewski |
| 4,328,594 A | 5/1982 | Campbell et al. |
| 4,442,554 A | 4/1984 | Copes |
| 4,506,395 A | 3/1985 | Haupt |
| 4,547,913 A | 10/1985 | Phillips |
| 4,606,332 A | 8/1986 | Gibson |
| 4,636,220 A | 1/1987 | Ziegelmeyer |
| 4,645,509 A | 2/1987 | Poggi et al. |
| 4,676,800 A | 6/1987 | Chen |
| 4,676,801 A | 6/1987 | Lundeen |
| 4,721,510 A | 1/1988 | Cooper et al. |
| 4,822,363 A | 4/1989 | Phillips |
| 4,865,611 A | 9/1989 | Al-Turaiki |
| 4,865,612 A | 9/1989 | Arbogast et al. |
| 4,938,775 A | 7/1990 | Morgan |
| 4,959,073 A | 9/1990 | Merlette |
| 5,019,109 A | 5/1991 | Voisin |
| 5,030,239 A | 7/1991 | Copes |
| 5,037,444 A | 8/1991 | Phillips |
| 5,062,859 A | 11/1991 | Naeder |
| 5,112,356 A | 5/1992 | Harris et al. |
| 5,116,383 A | 5/1992 | Shorter et al. |
| 5,116,384 A | 5/1992 | Wilson et al. |
| 5,156,632 A | 10/1992 | Wellershaus |
| 5,181,932 A | 1/1993 | Phillips |
| 5,181,933 A | 1/1993 | Phillips |
| 5,217,500 A | 6/1993 | Phillips |
| 5,219,365 A | 6/1993 | Sabolich |
| 5,258,039 A | 11/1993 | Goh et al. |
| 5,267,633 A | 12/1993 | Endo et al. |
| 5,290,319 A | 3/1994 | Phillips |
| 5,314,499 A | 5/1994 | Collier, Jr. |
| 5,376,133 A | 12/1994 | Grammes |
| 5,376,139 A | 12/1994 | Pitkin |
| 5,376,141 A | 12/1994 | Phillips |
| 5,387,246 A | 2/1995 | Phillips |
| 5,425,781 A | 6/1995 | Allard et al. |
| 5,425,782 A | 6/1995 | Phillips |
| 5,443,528 A | 8/1995 | Allen |
| 5,443,529 A | 8/1995 | Phillips |
| 5,458,656 A | 10/1995 | Phillips |
| 5,464,441 A | 11/1995 | Phillips |
| 5,482,513 A | 1/1996 | Wilson |
| 5,486,209 A | 1/1996 | Phillips |
| 5,507,838 A | 4/1996 | Chen |
| 5,509,936 A | 4/1996 | Rappoport et al. |
| 5,509,937 A | 4/1996 | Allard et al. |
| 5,509,938 A | 4/1996 | Phillips |
| 5,514,185 A | 5/1996 | Phillips |
| 5,514,186 A | 5/1996 | Phillips |
| 5,549,714 A | 8/1996 | Phillips |
| 5,571,210 A | 11/1996 | Lindh |
| 5,571,213 A | 11/1996 | Allen |
| 5,593,455 A | 1/1997 | Phillips |
| 5,593,456 A | 1/1997 | Merlette |
| 5,593,457 A | 1/1997 | Phillips |
| 5,653,767 A | 8/1997 | Allen et al. |
| 5,653,768 A | 8/1997 | Kania |
| 5,725,598 A | 3/1998 | Phillips |
| 5,728,175 A | 3/1998 | Rincoe |
| 5,728,176 A | 3/1998 | Phillips |
| 5,728,177 A | 3/1998 | Phillips |
| 5,746,774 A | 5/1998 | Kramer et al. |
| 5,766,265 A | 6/1998 | Phillips |
| 5,766,704 A | 6/1998 | Allen et al. |
| 5,769,896 A | 6/1998 | Rosendahl et al. |
| 5,776,205 A | 7/1998 | Phillips |
| 5,779,735 A | 7/1998 | Molino |
| 5,800,564 A | 9/1998 | Gelineau |
| 5,800,565 A | 9/1998 | Biedermann |
| 5,800,569 A | 9/1998 | Phillips |
| 5,824,112 A | 10/1998 | Phillips |
| 5,888,238 A | 3/1999 | Phillips et al. |
| 5,893,891 A | 4/1999 | Zahedi |
| 5,899,944 A | 5/1999 | Phillips |
| 5,913,902 A | 6/1999 | Geible |
| 5,944,760 A | 8/1999 | Christensen |
| 5,957,981 A | 9/1999 | Gramnas |
| 5,976,191 A | 11/1999 | Phillips |
| 5,993,488 A | 11/1999 | Phillips |
| 6,007,582 A | 12/1999 | May |
| 6,019,795 A | 2/2000 | Phillips |
| 6,071,313 A | 6/2000 | Phillips |
| 6,077,301 A | 6/2000 | Pusch |
| 6,099,572 A | 8/2000 | Mosler et al. |
| 6,120,547 A | 9/2000 | Christensen |
| 6,165,227 A | 12/2000 | Phillips |
| 6,187,052 B1 | 2/2001 | Molino et al. |
| 6,197,068 B1 | 3/2001 | Christensen |
| 6,206,934 B1 | 3/2001 | Phillips |
| 6,228,124 B1 | 5/2001 | Stemker et al. |
| 6,241,776 B1 | 6/2001 | Christensen |
| 6,254,643 B1 | 7/2001 | Phillips |
| 6,261,324 B1 | 7/2001 | Merlette |
| 6,280,479 B1 | 8/2001 | Phillips |
| 6,290,730 B1 | 9/2001 | Pitkin et al. |
| 6,306,178 B1 | 10/2001 | Kania et al. |
| 6,402,790 B1 | 6/2002 | Celebi |
| 6,406,500 B1 | 6/2002 | Phillips |
| 6,443,993 B1 | 9/2002 | Koniuk |
| 6,443,995 B1 | 9/2002 | Townsend et al. |
| 6,514,293 B1 | 2/2003 | Jang et al. |
| 6,562,075 B2 | 5/2003 | Townsend et al. |
| 6,596,029 B1 | 7/2003 | Gramnas |
| 6,602,295 B1 | 8/2003 | Doddroe et al. |
| 6,663,673 B2 | 12/2003 | Chirstensen |
| 6,676,708 B1 | 1/2004 | Laghi |
| 6,793,683 B1 | 9/2004 | Laghi |
| 6,869,451 B1 | 3/2005 | Laghi |
| 6,875,241 B2 | 4/2005 | Christensen |
| 6,875,242 B2 | 4/2005 | Christensen |
| 6,911,052 B2 | 6/2005 | Christensen |
| 6,929,665 B2 | 8/2005 | Christensen |
| 6,966,933 B2 | 11/2005 | Christensen |
| 7,347,877 B2 * | 3/2008 | Clausen et al. ............... 623/52 |
| 2002/0133237 A1 | 9/2002 | Christensen |
| 2003/0045944 A1 | 3/2003 | Mosler et al. |
| 2003/0191540 A1 | 10/2003 | Townsend et al. |
| 2004/0162623 A1 | 8/2004 | Phillips |

FOREIGN PATENT DOCUMENTS

| | | |
|---|---|---|
| DE | 295807 | 12/1916 |
| EP | 1340478 | 9/2003 |
| GB | 1191633 | 5/1970 |
| GB | 1550658 | 11/1976 |
| GB | 2244006 | 11/1991 |
| IT | 556381 | 2/1957 |
| RU | 2033772 | 4/1995 |
| SU | 560606 | 6/1977 |
| WO | WO03/003953 | 1/2003 |

OTHER PUBLICATIONS

Thomas, Susan et al. "Comparison of the Seattle Lite Foot and Genesis II prosthetic Foot during walking and running" American Academy of Orthotists and Prosthetists, www.oandp.org/jpo/library/2000_01_009.asp, vol. 12, No. 1 pp. 9-14, 2000.

* cited by examiner

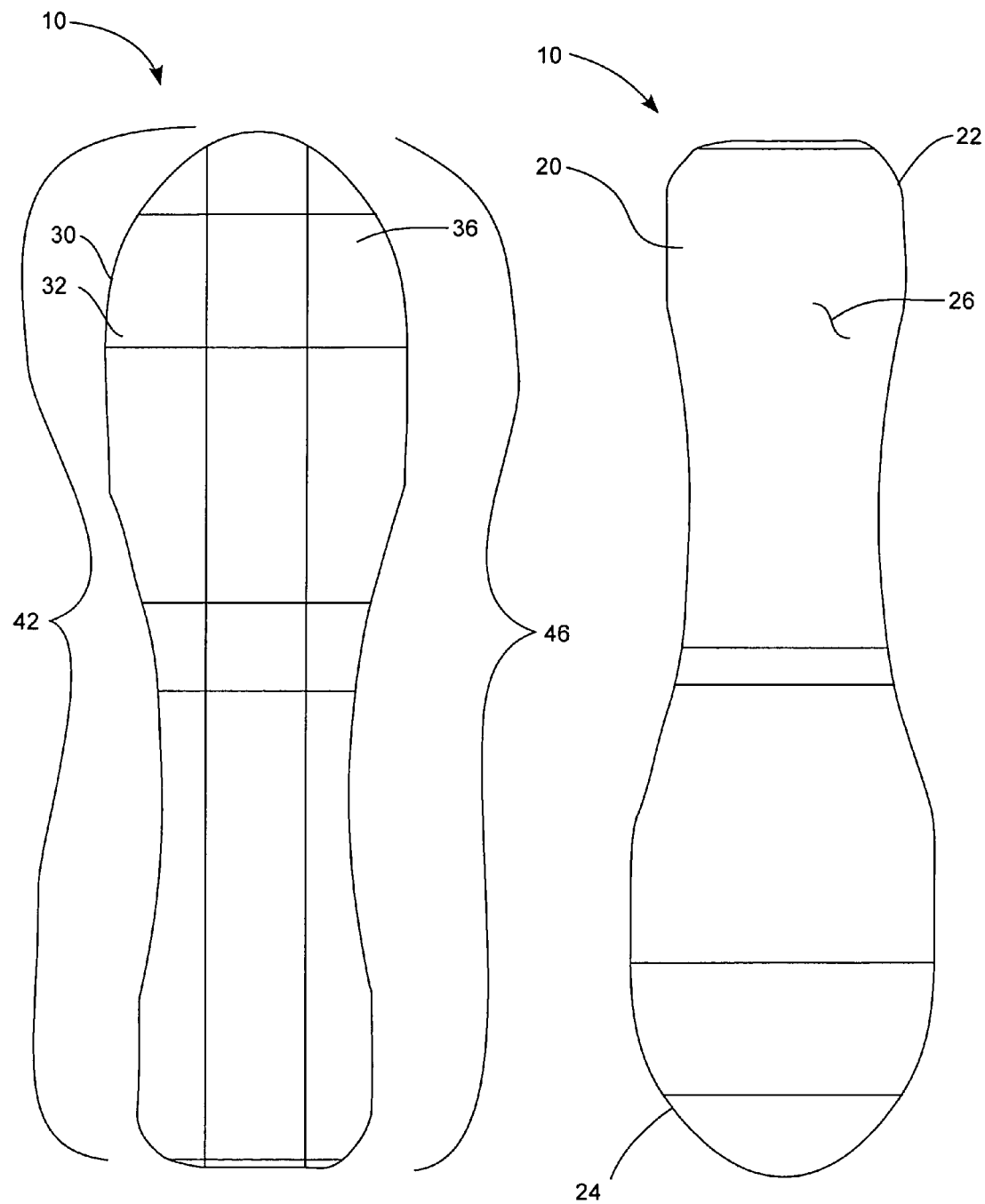

PROSTHETIC FOOT WITH VARIABLE MEDIAL/LATERAL STIFFNESS

BACKGROUND OF THE INVENTION

1. Field of the Invention

The present invention relates generally to a prosthetic foot with a variable stiffness sole plate.

2. Related Art

Many individuals have lost a limb for various reasons including war, accident, or disease. In most instances these individuals are not only able to live relatively normal lives, but physically active lives as well. Oftentimes, these individuals are aided in their everyday lives by a prosthetic limb. The objective of prosthesis is to provide an artificial limb that simulates the function and natural feel of the replaced limb.

With respect to prosthetic feet, the development of a functional and natural artificial foot has been limited by material and imagination. Many designs have attempted to copy the anatomy of the foot or simulate its actions by replacing the bones and muscle with various mechanical simulation by replacing the entire foot with an energy storage element such as a spring. As the user steps onto the foot, the user's weight compresses the spring. As the user moves forward, the user's weight comes off the foot and the energy stored in the spring is used to propel the user forward.

Almost all of the past designs have focused on the major aspect of the prosthetic foot movement of the ankle or foot as it relates to walking or running. Few designs consider the lateral, or side to side rotation of the foot when the foot is used on varied or uneven terrain. It will be appreciated that the forefoot of a natural foot rotates with a medial to lateral roll-over to accommodate variations in terrain. Most artificial feet of previous designs usually incorporate a unitary foot that is incapable of such movement.

Some designs have attempted to mimic the lateral rotation of the natural by splitting the forefoot region of the artificial foot longitudinally from the toe toward the heel, thereby effectively creating one or more "toes" on the prosthetic foot. This design is problematic, however, because the split creates at least two forefoot regions that can bend independent from one another and can result in an unnatural, out of balance feel to the user.

SUMMARY OF THE INVENTION

It has been recognized that it would be advantageous to develop a prosthetic foot with a variable stiffness foot plate for providing smooth and steady multi-axial rotation laterally across the forefoot region of the foot to allow the wearer to maneuver uneven terrain. Additionally, it has been recognized that it would be advantageous to develop a prosthetic foot with a variable stiffness foot plate for providing smooth and steady multi-axial rotation to assist with a natural medial to lateral roll-over of the prosthetic foot in response to uneven terrain.

In one aspect, the present invention provides a foot plate for a prosthetic foot. The foot plate can include a sole plate and a layer with laterally variable stiffness disposed above sole plate. The layer can have at least a medial portion and a lateral portion. The lateral portion can have a stiffness different than a stiffness of the medial portion. For example, the lateral portion can have a stiffness greater than a stiffness of the medial portion in order to provide a relatively softer instep and a relatively stiffer out-step.

In another aspect the present invention provides for a prosthetic foot device having a layer with laterally variable stiffness. The foot device can include a foot member that can be coupled to an amputee. The foot member can include an upper member having an attachment section configured to be coupled to a socket. The foot member can extend downwardly from the upper member to a toe section disposed at an approximate location of a toe of the user. The sole plate can be disposed below the foot member, and can have a heel section disposed at a natural location of a heel of a user and a toe section disposed at a natural location of a toe of the user.

In yet another aspect, the foot device can include a heel member disposed adjacent the foot member and a secondary heel member disposed adjacent the heel member.

Additional features and advantages of the invention will be apparent from the detailed description which follows, taken in conjunction with the accompanying drawings, which together illustrate, by way of example, features of the invention.

BRIEF DESCRIPTION OF THE DRAWINGS

FIG. 3 is top view of the foot plate of FIG. 1;

FIG. 4 is a bottom view of the foot plate of FIG. 1;

DETAILED DESCRIPTION

Figure 1:
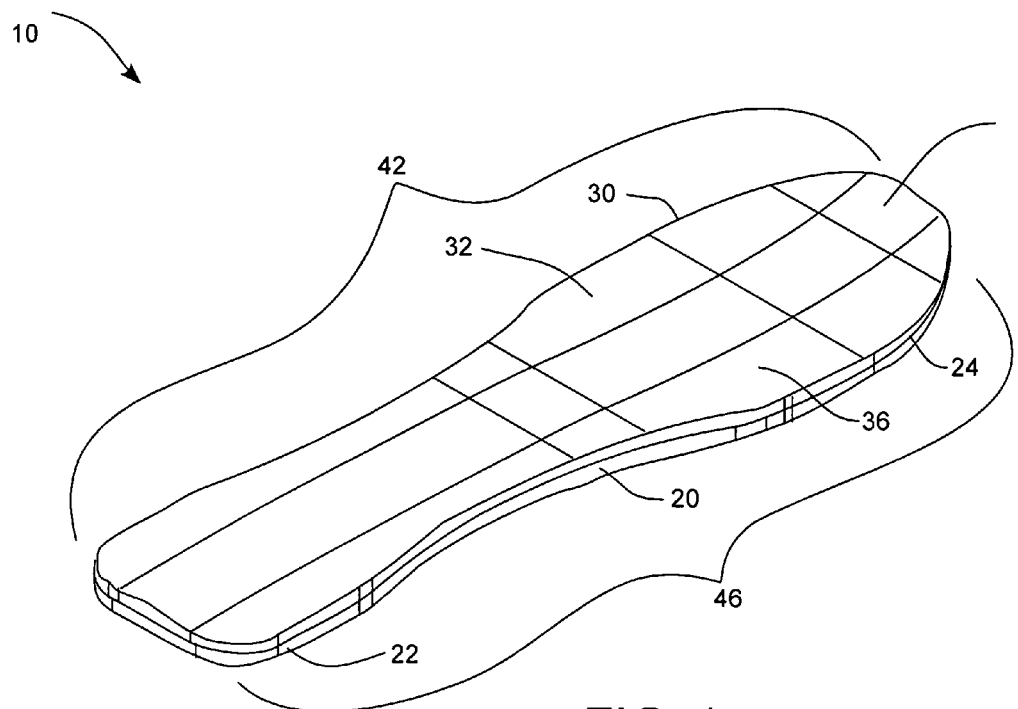
FIG. 1 is a perspective view of a foot plate having a layer with laterally variable stiffness in accordance with an embodiment of the present invention.
Figure 2:
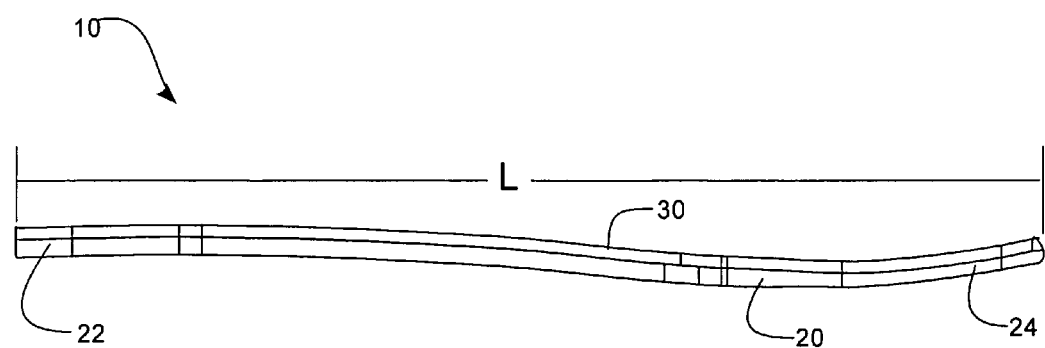
FIG. 2 is a side view of the foot plate of FIG. 1.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

The present invention relates generally to a foot plate for a prosthetic foot. The foot plate can have a variable stiffness across a forefoot portion of the footplate to provide a smooth and steady multi-axial rotation laterally across the forefoot region of the foot to allow the wearer to maneuver uneven terrain. The foot plate can have a sole plate and a layer with laterally variable stiffness disposed above sole plate. The layer can have at least a medial portion and a lateral portion. The medial portion can be located on or adjacent the instep, or inside of the foot plate. The lateral portion can be located on the out-step, or outside of the foot plate. The lateral portion can have stiffness greater than the stiffness of the medial portion to provide a relatively softer instep and a relatively stiffer out-step. Thus, the variable stiffness layer can provide smooth and steady multi-axial rotation to the foot plate in order to assist with a natural medial to lateral roll-over of the prosthetic foot in response to uneven terrain.

As illustrated in FIGS. 1-4, a prosthetic foot plate, indicated generally at 10, having a variable lateral stiffness is shown in accordance with an embodiment of the present invention, for use with a prosthetic foot. The foot plate can have a sole plate 20. The sole plate can have a heel section 22 disposed at an approximate natural location of a heel of a user and a toe section 24 disposed at a natural location of a toe of the user. The sole plate 20 can also include an energy storing spring 26 to store and release energy as the user steps on the ground. In one aspect, the energy storing spring 26 can be a leaf spring. For example, the sole plate 20 can be formed by a composite material, such as graphite fiber in a resin matrix, and can bend or flex to store energy, and can resiliently return to its original configuration to release energy.

The foot plate 10 can also have a layer 30 with laterally variable stiffness disposed above the sole plate 20. The layer 30 can have a medial portion 32 and a lateral portion 36. The medial portion 32 can be located on or adjacent the instep, or inside of the foot plate, as indicated generally at 42. The lateral portion 36 can be located on the out-step, or outside of the foot plate, as indicated generally at 46. The medial portion 32 and the lateral portion 36 can extend longitudinally for a length, L, of the foot plate 10.

The lateral portion 36 of the layer 30 can have a greater stiffness than the stiffness of the medial portion 32. In this way, the foot plate 10 of the present invention can provide a relatively softer instep and a relatively stiffer out-step as the user steps down onto a ground surface with a prosthetic foot having the foot plate 10. Advantageously, having a softer instep and stiffer out-step, as provided by the footplate 10, allows the foot plate to smoothly rotate and twist about multiple longitudinal axes of the foot plate 10 in response to variation or uneven surfaces in the terrain. This smooth and steady multi-axial rotation of the foot plate 10 can assist the wearer maintain balance and maneuver over uneven terrain by providing a natural medial to lateral roll-over of a prosthetic foot.

The layer 30 can also include at least one intermediate portion 34 that can be disposed between the medial and lateral portions 32 and 36. The intermediate portion 34 can have a greater stiffness than the medial portion 32 and the lateral portion 36. In this way, the medial portion 32 can rotate about a medial axis and the lateral portion 36 can rotate about a lateral axis. Additionally, the medial portion 32 and lateral portion 36 can both rotate about the stiffer intermediate portion 34. Thus, the intermediate portion 34 provides even greater maneuverability over uneven terrain because the less stiff medial portion 32 and lateral portion 36 can rotate in response to the terrain while the stiffer intermediate portion 34 maintains contact with the terrain. Additionally, the stiffer intermediate portion 34 can provide for a more natural medial to lateral roll-over of a prosthetic foot since the medial portion 32 and lateral portion 36 can rotate relatively independently from one but remain coupled to the stiffer intermediate portion 34.

The layer 30 with laterally variable stiffness can include a urethane material extending a length, L, of the medial portion 32, the lateral portion 36, and the intermediate portion 34. In one aspect, each of the medial portion 32, the lateral portion 36, and the intermediate portion 34 can be made from a urethane material, and can be bonded together to form a single urethane layer 30. Additionally, the urethane material of the intermediate portion 34 can have a greater durometer than the medial portion 32 and the lateral portion 36, and the lateral portion 36 can have a greater durometer than the medial portion 32. In this way, the stiffness of the medial portion 32 can be less than the stiffness of the intermediate portion 35 and the lateral portion 36, and the stiffness of the lateral portion 36 can be less than the stiffness of the intermediate portion 34.

Figure 5:
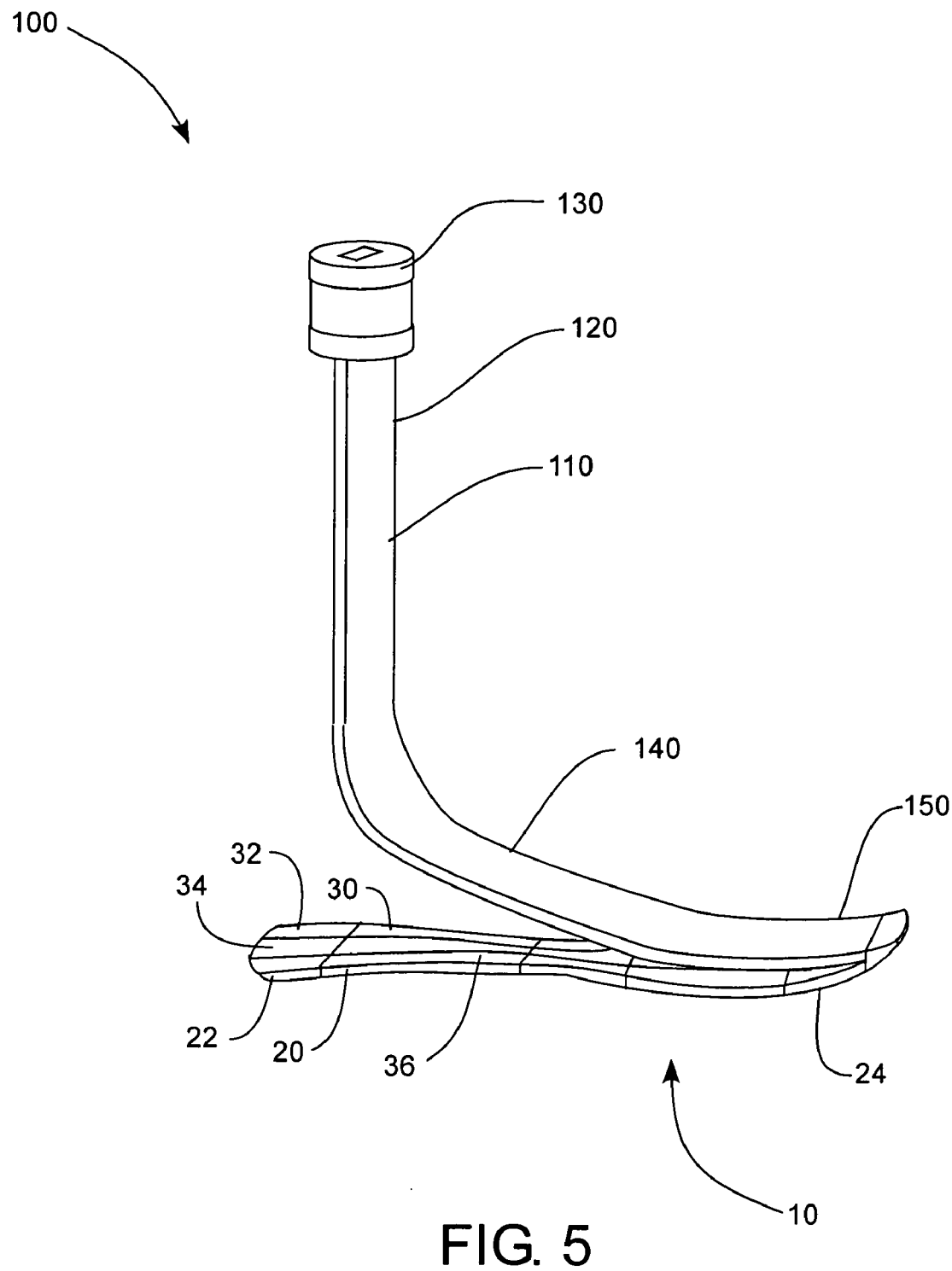
FIG. 5 is a perspective view of a prosthetic foot device including a sole plate having a layer with laterally variable stiffness in accordance with another embodiment of the present invention.

As illustrated in FIG. 5, a prosthetic foot device, indicated generally at 100, having a layer with laterally variable stiffness is shown in accordance with another embodiment of the present invention. The foot device 100 can include a foot plate 10 with a layer 30 having laterally variable stiffness, as described above and shown in FIGS. 1-4.

The foot device 100 can also include a foot member 110 that can be coupleable to an amputee. The foot member 110 can have an upper member 120 having an attachment section 130 that can be coupled to a socket of an amputee. The upper member 120 can extend downwardly from the attachment section 130 through an arch section 140 to a toe section 150. The arch section 140 can be located at an approximate natural location of an arch of a user and the toe section 150 can be located at an approximate natural location of a toe of a user.

The foot device 100 can also have a sole plate 20 disposed below the foot member 110. The sole plate 20 can have a heel section 22 disposed at an approximate natural location of a heel of a user and a toe section 24 disposed at a natural location of a toe of the user.

The sole plate 20 can also include a layer 30 with laterally variable stiffness. The layer 30 can be disposed above sole plate 20, and between the sole plate 20 and the foot member 110. The layer 30 can have a medial portion 32, a lateral portion 36, and an intermediate portion 34 between the medial and lateral portions. The lateral portion 36 can have a stiffness greater than the stiffness of the medial portion 32 to provide a relatively softer instep and a relatively stiffer out-step. The intermediate portion 34 can have a greater stiffness than the medial portion 32 and the lateral portion 36.

Figure 6:
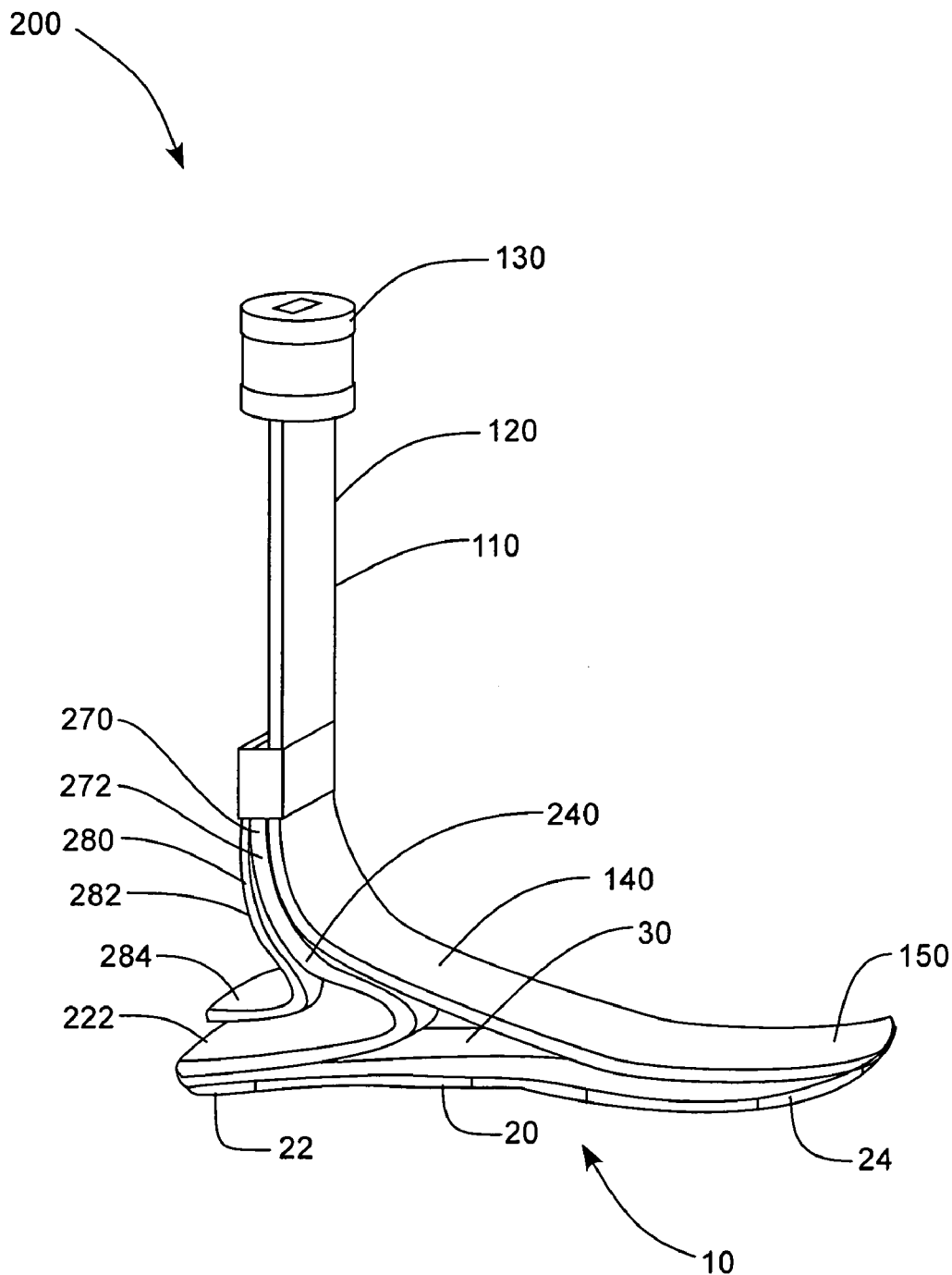
FIG. 6 is a perspective view of a prosthetic foot device including a sole plate having a layer with laterally variable stiffness in accordance with another embodiment of the present invention.

As illustrated in FIG. 6, a prosthetic foot device, indicated generally at 200, having a layer with laterally variable stiffness is shown in accordance with another embodiment of the present invention. The foot device 200 can include a foot plate 10 with a layer 30 having laterally variable stiffness, as described above and shown in FIGS. 1-4. Additionally, the foot device 200 can be similar in many respects to the foot device 100 described above and shown in FIG. 5.

The foot device 200 can also include a foot member 110 that can be coupleable to an amputee. The foot member 110 can be a primary foot member. The foot member 110 can have an upper member 120 having an attachment section 130 that can be coupled to a socket of an amputee. The upper member can extend downwardly from the attachment section through an arch section 140 to a toe section 150. The arch section 140 can be located at an approximate natural location of an arch of a user and the toe section can be located at an approximate natural location of a toe of a user.

The foot device can also have a sole plate 20 disposed below the foot member 110. The sole plate can have a heel section 22 disposed at an approximate natural location of a heel of a user and a toe section 24 disposed at a natural location of a toe of the user.

The sole plate 20 can also include a layer 30 with laterally variable stiffness, as discussed above and shown in FIGS. 1-4. The layer 30 can be disposed above sole plate 20 and can have a medial portion 32, a lateral portion 36, and an intermediate portion 34 between the medial and lateral portions. The lateral portion 36 can have a stiffness greater than the stiffness of the medial portion 32 to provide a relatively softer instep and a relatively stiffer out-step. The intermediate portion 34 can have a greater stiffness than the medial portion 32 and the lateral portion 36.

Returning to FIG. 6, the foot device 200 can also have a heel member 270 disposed adjacent the foot member 110. The heel member 270 can include an upper member 272 that can extend downwardly and forwardly to a location corresponding to an approximate arch location 240 of the user. The heel member 270 can extend rearwardly from the approximate arch 240 location to an approximate heel location 222 of the user. The heel member 280 can be engageable by the heel section 22 of the sole plate 20 at the approximate heel location 222 to provide additional resistance to the sole plate 20 when the user steps on the heel section 22 of the sole plate 20.

The foot device 200 can also include a secondary heel member 280 disposed adjacent the heel member 270 (or primary heel member). The secondary heel member 280 can include an upper member 282 that can extend downwardly to a location above the approximate heel location 240. The secondary heel member 280 can be engageable by the heel member 270 at the approximate heel location 284 to provide additional resistance to the heel member 270 when the user steps on the heel section 22 of the sole plate 20.

Figure 7:
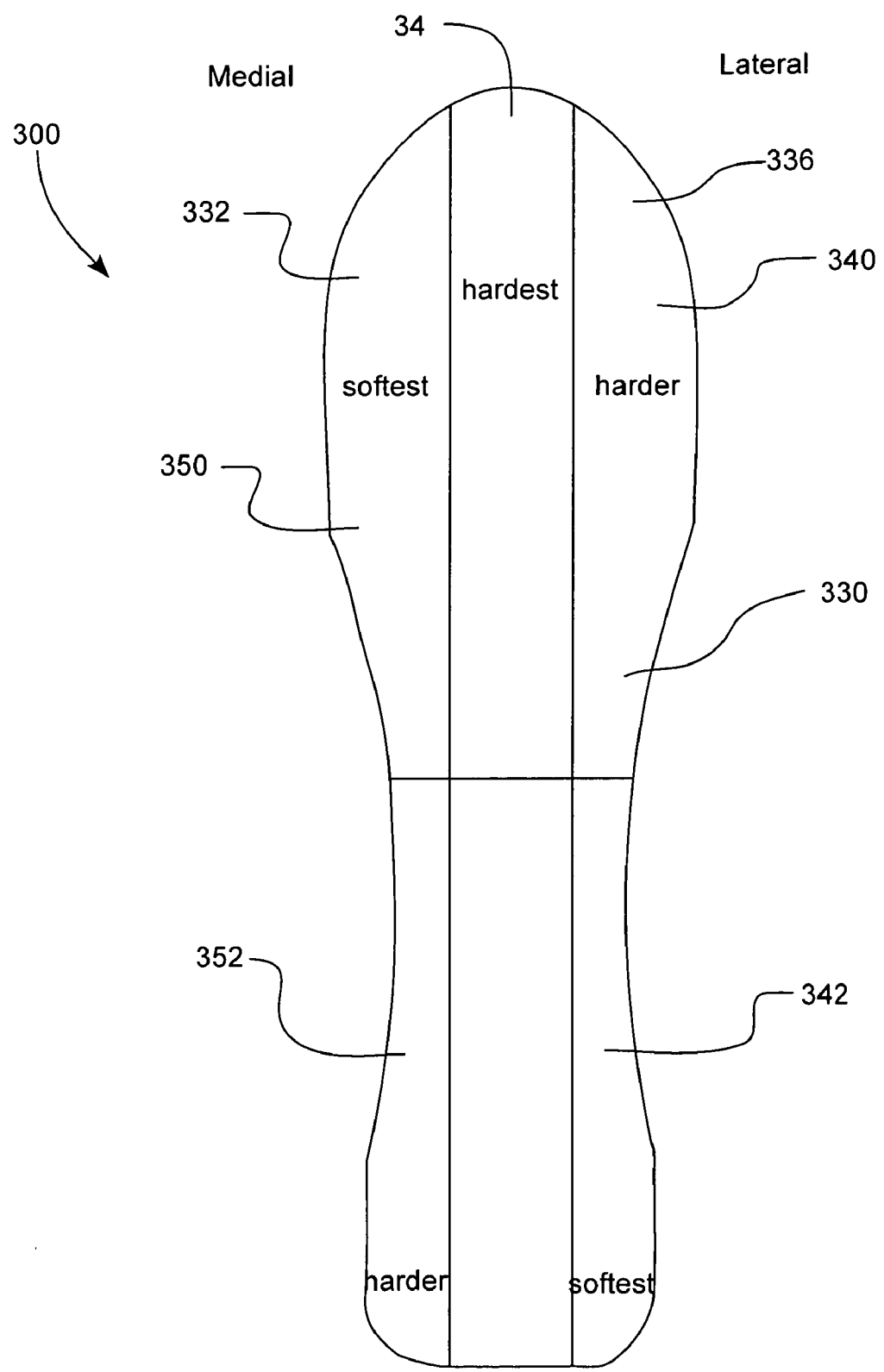
FIG. 7 is a top view of a foot plate having a layer with laterally and longitudinally variable stiffness in accordance with another embodiment of the present invention.

As illustrated in FIG. 7, a prosthetic foot plate, indicated generally at 300, having a variable lateral stiffness is shown in accordance with another embodiment of the present invention, for use with a prosthetic foot. The foot plate 300 can be similar in many respects to the foot plate 10 described above and shown in FIGS. 1-6. The foot plate 300 can have a sole plate 20, and a layer 330 with laterally variable stiffness disposed above the sole plate 20. The layer 330 can have a medial portion 332 and a lateral portion 336. The layer can also have an intermediate portion 34.

The lateral portion 336 can have a forward section 340 and a rearward section 342. The medial portion 332 can also have a forward section 350 and a rearward section 352. The stiffness of each of the forward sections 340 and 350 can be different than the stiffness of each of the rearward sections 342 and 352. Thus, in one aspect (shown in FIG. 7), the forward section 340 of the lateral portion 336 can have a greater stiffness than the rearward section 342 of the lateral portion 336. Likewise, the rearward section 352 of the medial portion 332 can have a greater stiffness than the forward section 350 of the medial portion 332. Additionally, in another aspect (not shown), the rearward section 342 of the lateral portion 336 can have a greater stiffness than the forward section 340 of the lateral portion 336. Similarly, the forward section 350 of the medial portion 332 can have a greater stiffness than the rearward section 352 of the medial portion 332.

Advantageously, having a variable stiffness longitudinally along the length of the foot as well as laterally across the width of the foot, as provided by the footplate 300, allows the foot plate to smoothly rotate and twist about multiple longitudinal and lateral axes of the foot plate 300 in response to variation or uneven surfaces in the terrain and also in response to dynamic movement of the foot by the user during strenuous physical activity. This smooth and steady multi-axial rotation of the foot plate 10 can assist the wearer maintain balance and maneuver over uneven terrain and during strenuous activity, such as running or hiking, by providing a natural medial to lateral roll-over of a prosthetic foot.

Various aspects of a prosthetic foot are disclosed in U.S. Pat. No. 6,929,665; and U.S. patent application Ser. No. 10/936,951, filed Sep. 8, 2004; and Ser. No. 11/109,320, filed Apr. 18, 2005; which are herein incorporated by reference.

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth herein.

What is claimed is:

1. A prosthetic foot device having a layer with laterally variable stiffness, the device comprising:
    a) a foot member, configured to be coupled to an amputee, including an upper member having an attachment section configured to be coupled to a socket, and extending downwardly therefrom;
    b) a heel member, disposed adjacent the foot member, including an upper member and extending downwardly and forwardly to a location corresponding to an approximate arch location of the user and rearwardly from the approximate arch location to an approximate heel location of the user;
    c) a sole plate, disposed below the foot member, and having a heel section disposed at a natural location of a heel of a user and a toe section disposed at a natural location of a toe of the user; and
    d) a layer with laterally variable stiffness, disposed above sole plate and having a medial portion, a lateral portion, and an intermediate portion between the medial and lateral portions;
    e) the lateral portion and the medial portion having different stiffness; and
    f) the intermediate portion having a greater stiffness than the medial and lateral portions.

2. A foot device in accordance with claim 1, wherein the sole plate further includes an energy storing leaf spring.

3. A foot device in accordance with claim 1, wherein the medial portion, the lateral portion and the intermediate portion extend longitudinally substantially an entire length of the foot plate.

4. A foot device in accordance with claim 1, wherein the layer with laterally variable stiffness includes a urethane material extending across the medial portion, the lateral portion and the intermediate portion.

5. A foot device in accordance with claim 4, wherein the urethane material of the intermediate portion has a greater durometer than the medial portion and the lateral portion, and wherein the lateral portion has a greater durometer than the medial portion.

6. A foot device in accordance with claim 1, further comprising:
    a secondary heel member disposed adjacent the heel member, including an upper member and extending downwardly therefrom to a location above the approximate heel location, the secondary heel member being engageable by the heel member at the approximate heel location to provide additional resistance to the heel member.

7. A prosthetic foot device having a layer with laterally variable stiffness, the device comprising:
    a) a foot member, configured to be coupled to an amputee, including an upper member having an attachment section configured to be coupled to a socket, and extending downwardly and forwardly therefrom to an approximate toe location of a user;
    b) a heel member, disposed adjacent the primary foot member, including an upper member extending downwardly and forwardly to a location corresponding to an approximate arch location of the user and rearwardly from the approximate arch location to an approximate heel location of the user;

c) a secondary heel member disposed adjacent the heel member, including an upper member and extending downwardly therefrom to a location above the approximate heel location, the secondary heel member being engageable by the heel member at the approximate heel location to provide additional resistance to the heel member; and d) a sole plate, disposed below the foot member and the heel member, and having a heel section disposed at the approximate heel location of the user and a toe section disposed at the approximate toe location of the user; and i) a layer with laterally variable stiffness, disposed above sole plate and having a medial portion, a lateral portion, and an intermediate portion between the medial and lateral portions;

ii) the lateral portion having a stiffness greater than the stiffness of the medial portion to provide a relatively softer instep and a relatively stiffer out-step; and iii) the intermediate portion having a greater stiffness than the medial and lateral portions.

8. A foot device in accordance with claim 7, wherein the sole plate further includes an energy storing leaf spring.

9. A foot device in accordance with claim 7, wherein the medial portion, the lateral portion and the intermediate portion extend longitudinally substantially an entire length of the foot plate.

10. A foot device in accordance with claim 7, wherein the layer with laterally variable stiffness includes a urethane material extending across the medial portion, the lateral portion and the intermediate portion.

11. A foot device in accordance with claim 10, wherein the urethane material of the intermediate portion has a greater durometer than the medial portion and the lateral portion, and wherein the lateral portion has a greater durometer than the medial portion.

12. A foot device in accordance with claim 7, wherein the lateral portion has a stiffness greater than a stiffness of the medial portion to provide a relatively softer instep and a relatively stiffer out-step.

13. A foot device in accordance with claim 7, wherein the medial portion and the lateral portion extend longitudinally substantially an entire length of the foot plate.

14. A foot device in accordance with claim 7, wherein the lateral portion and medial portion further include a forward section and a rearward section, and a stiffness of the forward section is different than a stiffness of the rearward section.

15. A foot device in accordance with claim 14, wherein the forward section of the lateral portion has a greater stiffness than the rearward section of the lateral portion, and the rearward section of the medial portion has a greater stiffness than the forward section of the medial portion.

16. A foot device in accordance with claim 14, wherein the rearward section of the lateral portion has a greater stiffness than the forward section of the lateral portion, and the forward section of the medial portion has a greater stiffness than the rearward section of the medial portion.

17. A foot device in accordance with claim 1, wherein the lateral portion has a stiffness greater than a stiffness of the medial portion to provide a relatively softer instep and a relatively stiffer out-step.

18. A foot device in accordance with claim 1, wherein the medial portion and the lateral portion extend longitudinally substantially an entire length of the foot plate.

19. A foot device in accordance with claim 1, wherein the lateral portion and medial portion further include a forward section and a rearward section, and a stiffness of the forward section is different than a stiffness of the rearward section.

20. A foot device in accordance with claim 19, wherein the forward section of the lateral portion has a greater stiffness than the rearward section of the lateral portion, and the rearward section of the medial portion has a greater stiffness than the forward section of the medial portion.

21. A foot device in accordance with claim 19, wherein the rearward section of the lateral portion has a greater stiffness than the forward section of the lateral portion, and the forward section of the medial portion has a greater stiffness than the rearward section of the medial portion.

* * * * *